United States Patent
Oohashi et al.

(10) Patent No.: US 9,737,636 B2
(45) Date of Patent: Aug. 22, 2017

(54) METHOD FOR PRODUCING LAMINATE OF SHEET-SHAPED CELL CULTURE AND FIBRIN GEL

(71) Applicants: TERUMO KABUSHIKI KAISHA, Shibuya-ku, Tokyo (JP); OSAKA UNIVERSITY, Suita-shi, Osaka (JP)

(72) Inventors: Fumiya Oohashi, Kanagawa (JP); Ryouhei Takeuchi, Kanagawa (JP); Tadashi Sameshima, Kanagawa (JP); Shigeru Miyagawa, Osaka (JP); Yoshiki Sawa, Osaka (JP); Atsuhiro Saito, Osaka (JP)

(73) Assignees: TERUMO KABUSHIKI KAISHA, Shibuya-Ku, Tokyo (JP); OSAKA UNIVERSITY, Suita-Shi, Osaka (JP)

( * ) Notice: Subject to any disclaimer, the term of this patent is extended or adjusted under 35 U.S.C. 154(b) by 0 days.

(21) Appl. No.: 14/844,259

(22) Filed: Sep. 3, 2015

(65) Prior Publication Data

US 2016/0058908 A1 Mar. 3, 2016

(30) Foreign Application Priority Data

Sep. 3, 2014 (JP) .................................. 2014-179150

(51) Int. Cl.
*A61L 27/34* (2006.01)
*A61L 27/38* (2006.01)
*A61L 27/58* (2006.01)
*A61L 27/22* (2006.01)
*A61L 27/52* (2006.01)

(52) U.S. Cl.
CPC ............. *A61L 27/58* (2013.01); *A61L 27/225* (2013.01); *A61L 27/38* (2013.01); *A61L 27/52* (2013.01); *A61L 2430/20* (2013.01)

(58) Field of Classification Search
None
See application file for complete search history.

(56) References Cited

FOREIGN PATENT DOCUMENTS

| JP | 2007-528755 A | 10/2007 |
| JP | 2011-172925 A | 9/2011 |
| WO | WO 2005/011524 A1 | 2/2005 |

*Primary Examiner* — Emily Cordas
(74) *Attorney, Agent, or Firm* — Buchanan Ingersoll & Rooney PC

(57) ABSTRACT

A laminate of a sheet-shaped cell culture is disclosed, which has excellent operability and is suitable for implantation. A method is disclosed for producing a laminate of a fibrin gel and a sheet-shaped cell culture, including a step of dripping a liquid containing fibrinogen onto an upper surface of a sheet-shaped cell culture, a step of spraying a liquid containing thrombin onto the surface, and a step of forming a fibrin gel layer on the surface by a reaction between fibrinogen and thrombin; and a laminate of a fibrin gel and a sheet-shaped cell culture produced by the method are disclosed.

19 Claims, 11 Drawing Sheets

METHOD FOR PRODUCING LAMINATE OF SHEET-SHAPED CELL CULTURE AND FIBRIN GEL

CROSS-REFERENCES TO RELATED APPLICATIONS

This application claims priority to Japanese Application No. 2014-179150 filed on Sep. 3, 2014, the entire content of which is incorporated herein by reference.

TECHNICAL FIELD

The present disclosure generally relates to a method for producing a laminate of a sheet-shaped cell culture and a fibrin gel, a laminate produced by the method, a pharmaceutical composition containing the laminate, and a method for treating a disease using the laminate.

BACKGROUND DISCUSSION

In recent years, for the repair of damaged tissues, attempts have been made to transplant various cells. For example, for the repair of cardiac muscle tissue damaged due to an ischemic heart disease such as angina pectoris, or myocardial infarction, attempts have been made to use fetal cardiomyocytes, skeletal myoblasts, mesenchymal stem cells, cardiac stem cells, and ES cells (See, Haraguchi et al., Stem Cells Transl Med., 2012 February; 1 (2): 136-41).

As part of such attempts, a cell structure formed using a scaffold and a sheet-shaped cell culture obtained by forming cells into a sheet have been developed. (See JP-T-2007-528755).

Applications of sheet-shaped cell cultures to treatment have been studied focusing on regenerative medicine, including the use of a cultured epidermal sheet for skin damage due to a burn, the use of a sheet-shaped corneal epithelial cell culture for corneal damage, and the use of a sheet-shaped oral mucosa cell culture for the endoscopic excision of esophageal cancer.

Sheet-shaped cell cultures can be highly useful in regenerative medicine. However, they can be brittle as they are, and wrinkling, earing, and the like often occur during isolation from a culture medium or in the following operations. Thus, it can be extremely difficult to perform operations like transfer, storage, and implantation. In order to solve such problems, a method in which a fibrinogen liquid and a thrombin liquid are simultaneously sprayed onto a sheet-shaped cell culture to form a support layer containing fibrin on the sheet-shaped cell culture, thereby producing a laminate of a sheet-shaped cell culture and fibrin, has been attempted (See, JP-A-2011-172925).

With respect to the laminate of a sheet-shaped cell culture and fibrin described in JP-A-2011-172925, it has been found that when the laminate is isolated from a culture medium, there may be the case where the laminate tears, the case where isolation is not possible, or the case where the support layer comes off the sheet-shaped cell culture, making it impossible to obtain a complete laminate, for example. It has also been found that when the support layer is thickened to solve such problems, the cell function can be inhibited.

SUMMARY

Accordingly, a sheet-shaped cell culture laminate is disclosed that does not have the problems disclosed above, has excellent operability, and is suitable for implantation. In addition, a method for producing the same, a pharmaceutical composition containing the laminate, and a method for treating a disease using the laminate are disclosed.

In accordance with an exemplary embodiment, for the formation of a fibrin gel layer on a sheet-shaped cell culture, when a liquid containing fibrinogen is first dripped onto a sheet-shaped cell culture, and then a liquid containing thrombin is sprayed, a fibrin gel layer formed by a reaction between fibrinogen and thrombin can firmly adhere to the sheet-shaped cell culture; and as a result, when the obtained laminate of a fibrin gel and a sheet-shaped cell culture is isolated from a container, the fibrin gel layer does not come off the sheet-shaped cell culture.

In accordance with an exemplary embodiment, a method is disclosed for producing a laminate of a fibrin gel and a sheet-shaped cell culture, including a step of dripping a liquid containing fibrinogen onto an upper surface of a sheet-shaped cell culture, a step of spraying a liquid containing thrombin onto the surface, and a step of forming a fibrin gel layer on the surface by a reaction between fibrinogen and thrombin.

In accordance with an exemplary embodiment of the method as disclosed, further including, after the step of forming a fibrin gel layer, a step of washing the laminate.

In accordance with an exemplary embodiment of the method as disclosed, further including, after the step of forming a fibrin gel layer, a step of trimming excess fibrin gel.

In accordance with an exemplary embodiment, a laminate of a fibrin gel and a sheet-shaped cell culture produced by the methods as disclosed herein.

In accordance with an exemplary embodiment, a pharmaceutical composition containing the laminate as disclosed herein.

In accordance with an exemplary embodiment, the pharmaceutical composition disclosed herein, for treating a disease associated with tissue abnormality.

In accordance with an exemplary embodiment, a method is disclosed for treating a disease associated with tissue abnormality in a subject, including administering an effective amount of the laminate according or the pharmaceutical composition according to a subject in need of treating a disease associated with tissue abnormality.

In accordance with an exemplary embodiment, a laminate produced by the method of the disclosure can be relatively strong, having excellent operability, can be relatively easy to apply to the affected area, and also does not make a significant operational difference depending on the skill of the user. Therefore, diseases can be reliably treated, and the spread and expand of regenerative medicine using the laminate can be expected. In addition, the laminate of the disclosure can be made of a biocompatible component, and thus can also be directly implanted at an implantation site, followed by the degradation of the fibrin gel in vivo, which can help eliminate the need of a further surgery or the need of using a special jig for the implantation of a sheet-shaped cell culture, for example, making sheet-shaped cell cultures much more convenient.

DETAILED DESCRIPTION

Figure 1:
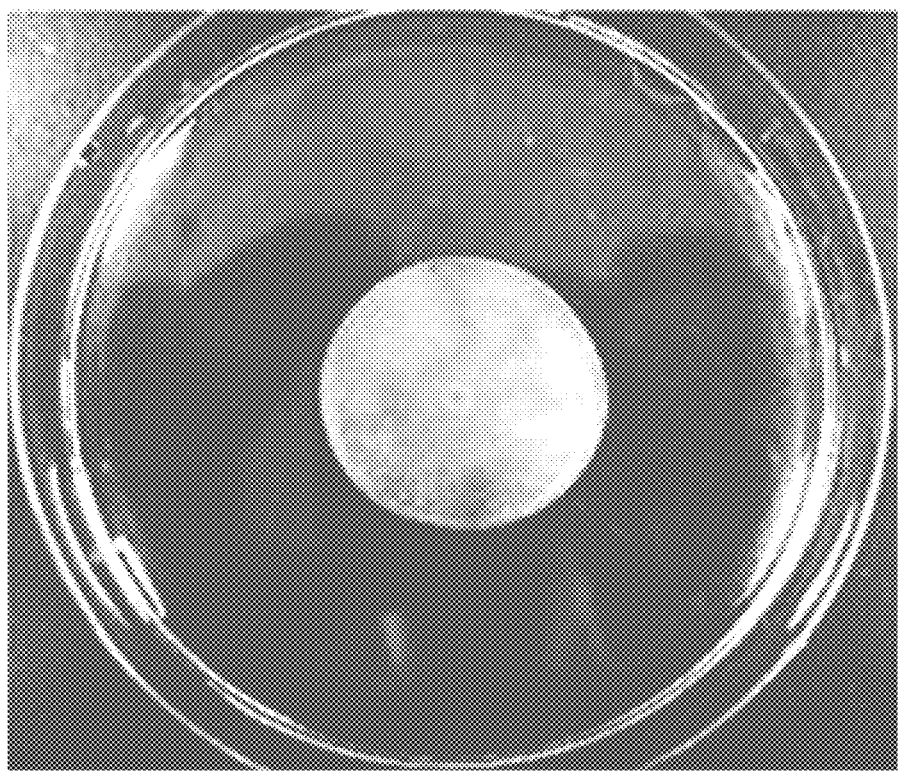
FIG. 1 is a photograph showing a sheet-shaped cell culture in a culture dish in accordance with an exemplary embodiment.

Unless defined otherwise, all technical and scientific terms used herein have the same meaning as commonly understood by one of ordinary skill in the art. All patents, applications, and other publications (including information available from the Internet) referred to herein are incorporated herein by reference in its entirety.

A method is disclosed for producing a laminate of a fibrin gel and a sheet-shaped cell culture, including a step of dripping a liquid containing fibrinogen onto an upper surface of a sheet-shaped cell culture, a step of spraying a liquid containing thrombin onto the surface, and a step of forming a fibrin gel layer on the surface by a reaction between fibrinogen and thrombin.

In the disclosure, "sheet-shaped cell culture" means cells connected to each other to form a sheet. Cells may be connected to each other directly (including connection through cell factors, such as adhesion molecules) and/or through an intervening substance. The intervening substance is not particularly limited as long as it is a substance that is capable of at least physically (mechanically) connecting cells, and may be an extracellular matrix, for example. Preferred examples of intervening substances include those derived from cells, for example, particularly those derived from cells forming the cell culture. Cells are at least physically (mechanically) connected, and may further be functionally connected, such as chemically or electrically, for example. The sheet-shaped cell culture may be composed of one cell layer (monolayer) or may also be composed of two or more cell layers (laminated (multilayer), for example, two layers, three layers, four layers, five layers, and six layers).

In accordance with an exemplary embodiment, it can be preferable that the sheet-shaped cell culture does not contain a scaffold (support). Scaffolds are sometimes used in this technical field to maintain the physical unity of a sheet-shaped cell culture by attaching cells to the surface and/or inside thereof. For example, a film made of polyvinylidene difluoride (PVDF) is known. However, the sheet-shaped cell culture in the disclosure may be capable of maintaining the physical unity even without such a scaffold. In addition, it can be preferable that the sheet-shaped cell culture is made only of a substance derived from cells forming the cell culture and does not contain other substances.

Cells forming the sheet-shaped cell culture are not particularly limited as long as they are capable of forming a sheet-shaped cell culture, and examples thereof include adherent cells (adhesive cells). Examples of adherent cells can include adhesive somatic cells (for example, cardiomyocytes, fibroblasts, epithelial cells, endothelial cells, hepatocytes, pancreatic cells, renal cells, adrenal cells, periodontal ligament cells, gingival cells, periosteal cells, skin cells, synoviocytes, and chondrocytes) and stem cells (for example, tissue stem cells such as myoblasts, cardiac stem cells, multipotential stem cells such as embryonic stem cells, iPS (induced pluripotent stem) cells, and mesenchymal stem cells). Somatic cells may be differentiated from stem cells, particularly iPS cells. Non-limiting examples of cells forming the sheet-shaped cell culture include myoblasts (for example, skeletal myoblasts), mesenchymal stem cells (for example, those derived from bone marrow, fat tissue, peripheral blood, skin, hair root, muscle tissue, endometrium, placenta, and umbilical cord blood), cardiomyocytes, fibroblasts, cardiac stem cells, embryonic stem cells, iPS cells, synoviocytes, chondrocytes, epithelial cells (for example, oral mucosa epithelial cells, retinal pigment epithelial cells, nasal mucosa epithelial cells), endothelial cells (for example, vascular endothelial cells), hepatocytes (for example, hepatic parenchymal cells), pancreatic cells (for example, islet cells), renal cells, adrenal cells, periodontal ligament cells, gingival cells, periosteal cells, and skin cells.

In accordance with an exemplary embodiment, cells forming the sheet-shaped cell culture may be derived from any organism that allows for treatment with the sheet-shaped cell culture. Such organisms are not limited, and examples thereof include humans, nonhuman primates, dogs, cats, pigs, horses, goats, sheep, rodent animals (for example, mice, rats, hamsters, and guinea pigs), and rabbits. In addition, the cells forming the sheet-shaped cell culture may be one kind of cells, and it is possible to use two or more kinds of cells. In a preferred embodiment of the disclosure, in the case two or more kinds of cells are used to form a sheet-shaped cell culture, the proportion (purity) of the predominant cells can be, for example, 60% or more, preferably 70% or more, and more preferably 75% or more, at the time of the completion of the production of the sheet-shaped cell culture.

The cells forming the sheet-shaped cell culture may be cells derived from a different species or cells derived from the same species. Here, "cells derived from a different species" means that in the case where the sheet-shaped cell culture is used for implantation, the cells are derived from an organism of a different species from the recipient. For example, in the case where the recipient is a human, the cells derived from a different species are cells derived from a monkey or a pig, for example. In addition, "cells derived from the same species" means that the cells are derived from an organism of the same species as the recipient. For example, in the case where the recipient is a human, the cells derived from the same species are human cells. Cells derived from the same species can include self-derived cells (also referred to as self-cells or autologous cells), for example, cells derived from the recipient, and non-self-derived cells of the same species (referred to as heterologous cells). Self-derived cells do not cause a rejection reaction when implanted, and thus are preferable in the disclosure. However, cells derived from a different species and non-self-derived cells of the same species can be used. In the case where cells derived from a different species or non-self-derived cells of the same species are used, immunosuppressive treatment may be required in order to suppress the rejection reaction. Incidentally, as used herein, cells other than self-derived cells, for example, cells derived from a different species and non-self-derived cells of the same species, may be collectively referred to as non-self-derived cells. In an exemplary embodiment of the disclosure, the cells can be autologous cells or heterologous cells. In an exemplary embodiment of the disclosure, the cells can be autologous cells. In another exemplary embodiment mode of the disclosure, the cells can be heterologous cells.

The sheet-shaped cell culture can be produced by known methods (see, for example, JP-T-2007-528755, JP-A-2011-172925, JP-A-2010-081829, JP-A-2011-110368). A method for producing a sheet-shaped cell culture can include, but is not limited to, a step of seeding cells on a culture medium, a step of forming the seeded cells into a sheet, and a step of isolating the sheet-shaped cell culture from the culture medium. Before the step of seeding cells on a culture medium, a step of freezing cells and a step of thawing cells may also be performed. Further, after the step of thawing cells, a step of washing cells may also be performed. These steps may each be performed by any known technique suitable for the production of a sheet-shaped cell culture. The production method of the disclosure may further include a step of producing a sheet-shaped cell culture. In that case, the step of producing a sheet-shaped cell culture may include one or more of the above sub-steps.

The liquid containing fibrinogen (hereinafter sometimes referred to as fibrinogen liquid) is not particularly limited as long as it is capable of reacting with thrombin to form a fibrin gel. Examples thereof include liquids containing fibrinogen at concentrations of, for example, 1 mg/mL to 500 mg/mL, 5 mg/mL to 400 mg/mL, 10 mg/mL to 250 mg/mL, 20 mg/mL to 150 mg/mL, 40 mg/mL to 100 mg/mL, and 50 mg/mL to 90 mg/mL. The solvent of the fibrinogen liquid is typically water. The fibrinogen liquid may also contain, in addition to fibrinogen, other components such as Factor XIII, aprotinin, serum albumin, glycine, L-arginine hydrochloride, L-isoleucine, monosodium L-glutamate, D-mannitol, sodium citrate hydrate, and sodium chloride. Fibrinogen liquids are commercially available, but may also be produced based on a known technique. Commercially available fibrinogen liquids are not limited, and examples thereof include a solution of the content of Vial 1 (a lyophilized powder of fibrinogen) of tissue adhesive BOL-HEAL® (manufactured by Teijin Pharma Ltd.) dissolved in the content of Vial 2 (a fibrinogen solution) and a solution of the content of Vial 1 (a fibrinogen powder) of tissue adhesive Beriplast® Combi-Set (manufactured by CSL Bering) dissolved in the content of Vial 2 (an aprotinin solution).

The dripping of the fibrinogen liquid may be performed using known techniques, such as a syringe or a pipet. As a syringe, for example, a needle-less syringe having a volume of 0.5 mL to 5 mL, a needle-equipped syringe (for example, a syringe equipped with a needle of 18 G to 27 G), the two-component mixing set of the preparation set attached to tissue adhesive BOLHEAL® (equipped with an application nozzle about 1 mm in inner diameter, manufactured by Nipro Corporation), or the two-component mixing set of the preparation set of Beriplast (equipped with an application nozzle, manufactured by Nipro Corporation) can be used. The dripping amount of the fibrinogen liquid is not particularly limited as long as the upper surface of the sheet-shaped cell culture can be covered, and may be, for example, about 6 $\mu L/cm^2$ to about 70 $\mu L/cm^2$, about 9 $\mu L/cm^2$ to about 50 $\mu L/cm^2$, about 12 $\mu L/cm^2$ to about 45 $\mu L/cm^2$, about 15 $\mu L/cm^2$ to about 40 $\mu L/cm^2$, or about 18 $\mu L/cm^2$ to about 32 $\mu L/cm^2$. Non-limiting examples of fibrinogen liquid dripping amounts can include, for example, relative to a 45-mm-diameter sheet-shaped cell culture, about 100 $\mu L$ to about 1000 $\mu L$, about 150 $\mu L$ to about 800 $\mu L$, about 200 $\mu L$ to about 700 $\mu L$, about 250 $\mu L$ to about 600 $\mu L$, and about 300 $\mu L$ to about 500 $\mu L$. The particle size of droplets of the fibrinogen liquid during dripping is not particularly limited, and may be, for example, within a range such that the diameter of droplets adhering to the sheet-shaped cell culture after dripping will be, for example, about 0.2 cm to about 2.0 cm. In addition, the weight of the droplets is not limited, and may be, for example, within a range of about 10 mg to about 100 mg, about 15 mg to about 50 mg, or about 20 mg to about 30 mg. The particle size and weight of droplets may be suitably adjusted by selecting whether the syringe is equipped with a needle, the gauge of the applied needle, or the shape of the needle tip.

The liquid containing thrombin (hereinafter sometimes referred to as thrombin liquid) is not particularly limited as long as it is capable of reacting with fibrinogen to form a fibrin gel. Examples thereof include liquids containing thrombin at concentrations of, for example, 1 unit/mL to 10000 units/mL, 10 units/mL to 5000 units/mL, 25 units/mL to 2500 units/mL, 50 units/mL to 1000 units/mL, 100 units/mL to 500 units/mL, and 250 units/mL to 300 units/mL. The solvent of the thrombin liquid is typically water. The thrombin liquid may also contain, in addition to thrombin, other components such as sodium citrate hydrate, and sodium chloride. Thrombin liquids are commercially available, but may also be produced based on a known technique. Commercially available thrombin liquids are not limited, and examples thereof include a solution of the content of Vial 3 (a lyophilized powder of thrombin) of tissue adhesive BOLHEAL® (manufactured by Teijin Pharma Ltd.) dissolved in the content of Vial 4 (a thrombin solution) and a solution of the content of Vial 3 (a thrombin powder) of tissue adhesive Beriplast® Combi-Set (manufactured by CSL Bering) dissolved in the content of Vial 4 (an calcium chloride solution).

The spraying of the thrombin liquid may be performed using known techniques, such as a spray. Non-limiting examples of such sprays include BOLHEAL® spray set (manufactured by Akita Sumitomo Bakelite Co., Ltd) and the two-component mixing set attached to tissue adhesive Beriplast® Combi-Set (manufactured by CSL Bering) equipped with a spray chip. The spraying amount of the thrombin liquid is not particularly limited as long as the upper surface of the sheet-shaped cell culture can be covered, and may be, as an estimated adhesion amount to the sheet-shaped cell culture, for example, about 3 µL/cm$^2$ to about 70 µL/cm$^2$, about 5 µL/cm$^2$ to about 50 µL/cm$^2$, about 6 µL/cm$^2$ to about 45 µL/cm$^2$, about 12 µL/cm$^2$ to about 40 µL/cm$^2$, or about 18 µL/cm$^2$ to about 32 µL/cm$^2$. Non-limiting examples of thrombin liquid spraying amounts include, as estimated adhesion amounts to a 45-mm-diameter sheet-shaped cell culture, for example, about 50 µL to about 1000 µL, about 80 µL to about 800 µL, about 100 µL to about 700 µL, about 200 µL to about 600 µL, and about 300 µL to about 500 µL. Incidentally, the estimated adhesion amount to a sheet-shaped cell culture can be calculated as follows: a predetermined amount of thrombin liquid is sprayed employing a spray, a height, a spray pressure, and a spray angle that are to be used for actual spraying, and the weight of the liquid adhering to a predetermined region (for example, within a 45-mm-diameter circle) is measured and divided by the density of the thrombin liquid (0.999973 g/cm$^3$).

In accordance with an exemplary embodiment, spraying conditions can be determined that will result in the desired estimated adhesion amount of the thrombin liquid based on the descriptions herein without requiring undue experimentation. For example, in Example 1 below, it is described that estimated adhesion amounts corresponding to spraying amounts of, for example, 300 µL, 500 µL, 600 µL, and 900 µL are 100 µL, 180 µL, 300 µL, and 450 µL, respectively. Accordingly, by the least squares method, an approximate curve is obtained as follows: estimated adhesion amount (µL)=spraying amount (µL)×0.6−88 (µL). Based on this, a spraying amount that results in the desired estimated adhesion amount can be determined. The spraying of the thrombin liquid is not particularly limited as long as the thrombin liquid can adhere to the upper surface, preferably uniformly all over the upper surface, of a sheet-shaped cell culture. For example, spraying can performed from a height of, for example, about 2 cm to about 15 cm at a spray angle of about 15° to about 150° at a pressure of about 0.005 MPa to about 0.1 MPa.

The ratio between the fibrinogen liquid and thrombin liquid applied to the sheet-shaped cell culture is not particularly limited as long as the operation of implanting the obtained laminate is not excessively inhibited. For example, as the volume ratio between the dripping amount of the fibrinogen liquid and the estimated adhesion amount of the thrombin liquid, it may be, for example, about 5:1 to about 1:3, about 4:1 to about 1:2, about 3:1 to about 1:1.5, about 2.5:1 to about 1:1, about 2:1 to about 1:1, or about 1.5:1 to about 1:1, and may particularly be about 1:1. In addition, as the ratio (mg:unit) between fibrinogen and thrombin adhering to the laminate, it may be, for example, about 8:5 to about 8:75, about 32:25 to about 4:25, about 24:25 to about 16:75, about 4:5 to about 8:25, about 16:25 to about 8:25, about 12:25 to about 8:25, and may particularly be about 8:25.

By adjusting the concentrations and amounts of the fibrinogen liquid and the thrombin liquid, the thickness of the resulting laminate and its properties (for example, flexibility and adhesiveness) can be changed. For example, by increasing the amount of the fibrinogen liquid, the thickness of the laminate can be increased. As the volume ratio between the dripping amount of the fibrinogen liquid (80 mg/mL) and the estimated adhesion amount of the thrombin liquid (250 units/mL) approaches 1:1, and as the ratio (mg:unit) between fibrinogen and thrombin adhering to the laminate approaches 8:25, the flexibility and adhesiveness of the laminate increase, resulting in improved operability.

The step of forming a fibrin gel layer is not limited, and may be performed, for example, by allowing the sheet-shaped cell culture to stand for a given period of time after spraying the thrombin liquid. The standing time is not limited, and may be, for example, about 1 minute to about 60 minutes, about 2 minutes to about 30 minutes, about 3 minutes to about 20 minutes, or about 4 minutes to about 10 minutes. More specifically, it may be, for example, about 1 minute, about 2 minutes, about 3 minutes, about 4 minutes, about 5 minutes, about 6 minutes, about 7 minutes, about 8 minutes, about 9 minutes, or about 10 minutes, and may particularly be about 5 minutes.

After the step of forming a fibrin gel layer, a step of washing the laminate may be performed. Washing may be performed by adding a predetermined amount of washing liquid to the container containing the laminate, and then discarding the same. Examples of washing liquids include, but are not limited to, water, physiological saline, various buffers (for example, PBS, and HBSS), and various liquid media (for example, DMEM, MEM, F12, DME, RPMI1640, MCDB (MCDB102, 104, 107, 120, 131, 153, and 199), L15, SkBM, RITC80-7, and DMEM/F12). The washing step can be performed once or more. In addition, the washing liquid added to the container may be discarded immediately, or may also be allowed to stand for a predetermined period of time (for example, without being limited thereto, for example, about 1 minute to about 60 minutes, about 5 minutes to about 30 minutes, or about 10 minutes to about 20 minutes, and particularly about 15 minutes) and then discarded.

After the step of forming a fibrin gel layer (in the case where a step of washing a laminate is included, after the washing step), as necessary, a step of trimming excess fibrin gel may be performed. Trimming may be performed using any instrument that can be used for cutting a gel-like substance. Examples of such instruments include, but are not limited to, scalpels, scissors, and surgical knives. The fibrin gel may be trimmed along the outline of the sheet-shaped cell culture, or may also be trimmed such that the fibrin gel protrudes around the sheet-shaped cell culture, for example, such that the margin of the laminate is made only of a fibrin gel.

The step of dripping a liquid containing fibrinogen, step of spraying a liquid containing thrombin, step of forming a fibrin gel layer, step of washing a laminate, and/or step of trimming excess fibrin gel mentioned above may be performed on a sheet-shaped cell culture still adhering to the culture medium, or may also be performed on a sheet-shaped cell culture that has been isolated from the culture medium.

In an exemplary embodiment of the production method of the disclosure, all the steps are performed in vitro. In another exemplary embodiment, the production method of the disclosure is not limited to steps performed in vivo, and may include, for example, a step of collecting cells or a cell source tissue from a subject. In one exemplary embodiment of the production method of the disclosure, all the steps are performed under aseptic conditions. In an exemplary embodiment, the production method of the disclosure is performed such that the laminate finally obtained will be substantially aseptic. In an exemplary embodiment, the production method of the disclosure is performed such that the laminate finally obtained will be aseptic.

Another aspect of the disclosure relates to a laminate of a sheet-shaped cell culture and a fibrin gel produced by the production method of the disclosure. As compared with, for example, a laminate produced by simultaneously spraying a fibrinogen liquid and a thrombin liquid onto a sheet-shaped cell culture as described in JP-A-2011-172925, in the laminate of the disclosure, the adhesion of the fibrin gel layer to the sheet-shaped cell culture is stronger, and the fibrin gel layer does not come off the sheet-shaped cell culture during operation. In accordance with an exemplary embodiment, it is believed that in the laminate of the disclosure, before reacting with thrombin to form fibrin, fibrinogen permeates inside the sheet-shaped cell culture (for example, intercellular space), whereby a fibrin gel is three-dimensionally bound to the sheet-shaped cell culture and anchored, while the area of contact between the fibrin gel and the sheet-shaped cell culture is increased, resulting in firm adhesion between the two. In contrast, with respect to the laminate described in JP-A-2011-172925, it is believed that fibrinogen and thrombin simultaneously come into contact with a sheet-shaped cell culture and immediately react to form a fibrin gel; as a result, the fibrin gel is unlikely to form such a three-dimensional bond with the sheet-shaped cell culture. Therefore, it is believed that the laminate of the disclosure is different from the laminate described in JP-A-2011-172925 both in quality and structure.

The strength of the laminate is not limited. For example, as measured by the method described in Example 2, it may be about 0.010 N or more, about 0.015 N or more, about 0.020 N or more, about 0.025 N or more, about 0.030 N or more, about 0.035 N or more, about 0.040 N or more, or about 0.045 N or more, and may also be within a range of about 0.010 N to about 0.200 N, about 0.015 N to about 0.100 N, or about 0.020 N to about 0.50 N. In addition, the strength of the laminate may be, as compared with a sheet-shaped cell culture that is the same as one contained in the laminate except that a fibrin gel is not laminated, for example, about 1.5 times or more, about 2 times or more, about 3 times or more, about 4 times or more, about 5 times or more, about 6 times or more, about 7 times or more, about 8 times or more, about 9 times or more, or about 10 times or more the strength of such a sheet-shaped cell culture, for example, and may also be within a range of about 1.5 times to about 20 times, about 2 times to about 15 times, or about 2.5 times to about 10 times, for example.

In addition, the margin of the laminate may be made of the fibrin gel and the sheet-shaped cell culture laminated together, or may also be made of the fibrin gel alone or the sheet-shaped cell culture alone.

Another aspect of the disclosure relates to a laminate of a sheet-shaped cell culture and a fibrin gel, which has a reinforcing portion made of a fibrin gel (hereinafter sometimes referred to as reinforced laminate). The reinforced laminate of the disclosure has at least one reinforcing portion formed by further laminating a fibrin gel on the fibrin gel layer of the laminate of a sheet-shaped cell culture and a fibrin gel. By forming the reinforcing portion, the strength of a necessary part can be increased without increasing the entire thickness of the laminate. The reinforcing portion can be used as a suture insertion portion, a portion to be held with tweezers, for example. The reinforcing portion is formed by dripping a fibrinogen liquid and a thrombin liquid onto a fibrin gel layer. Various thicknesses and shapes can be made by adjusting the dripping amount, the dripping position, or the dripping pattern. For example, when a fibrinogen liquid (80 mg/mL) and a thrombin liquid (250 units/mL) are dripped each in an amount of 50 μL, a reinforcing portion having a base area of about 1 cm²×a height of about 1 mm to 2 mm can be obtained, while when they are dripped each in an amount of 100 μL, a reinforcing portion having a base area of about 1 cm²×a height of about 2 mm to 3 mm can be obtained.

The ratio between the fibrinogen liquid and thrombin liquid dripped is not particularly limited as long as a reinforcing portion having desired strength can be obtained. For example, as the volume ratio between the fibrinogen liquid and thrombin liquid dripped, it may be about 5:1 to about 1:3, about 4:1 to about 1:2, about 3:1 to about 1:1.5, about 2.5:1 to about 1:1, about 2:1 to about 1:1, or about 1.5:1 to about 1:1, and may particularly be about 1:1. In addition, as the ratio (mg:unit) between fibrinogen and thrombin contained in the reinforcing portion, for example, it may be about 8:5 to about 8:75, about 32:25 to about 4:25, about 24:25 to about 16:75, about 4:5 to about 8:25, about 16:25 to about 8:25, or about 12:25 to about 8:25, and may particularly be about 8:25.

The strength of the reinforcing portion is not limited. For example, as measured by the method described in Example 2, it may be about 0.04 N or more, about 0.05 N or more, about 0.06 N or more, about 0.07 N or more, about 0.08 N or more, about 0.09 N or more, about 0.10 N or more, about 0.12 N or more, or about 0.15 N or more, and may also be within a range of about 0.04 N to about 0.50 N, about 0.05 N to about 0.40 N, about 0.06 N to about 0.30 N, or about 0.07 N to about 0.25 N. In addition, the strength of the reinforcing portion may be about 1.5 times or more, about 2 times or more, about 3 times or more, about 4 times or more, about 5 times or more, about 6 times or more, about 7 times or more, about 8 times or more, about 9 times or more, or about 10 times or more the strength of a non-reinforcing portion, for example, and may also be within a range of about 1.5 times to about 25 times, about 2 times to about 20 times, about 3 times to about 15 times, or about 4 times to about 10 times, for example.

Another aspect of the disclosure relates to a method for producing a laminate of a sheet-shaped cell culture and a fibrin gel having a reinforcing portion made of a fibrin gel, the method can include a step of dripping a liquid containing fibrinogen onto an upper surface of a sheet-shaped cell culture, a step of spraying a liquid containing thrombin onto the surface, a step of forming a fibrin gel layer on the surface by a reaction between fibrinogen and thrombin, a step of dripping a liquid containing thrombin and a liquid containing fibrinogen onto the fibrin gel layer in such a manner that the two liquids are mixed on the fibrin gel layer, and a step of forming a reinforcing portion made of a fibrin gel on the fibrin gel layer by a reaction between fibrinogen and thrombin.

The step of dripping a liquid containing fibrinogen onto an upper surface of a sheet-shaped cell culture, the step of spraying a liquid containing thrombin onto the surface, the step of forming a fibrin gel layer on the surface by a reaction between fibrinogen and thrombin, the liquid containing thrombin, and the liquid containing fibrin are as described above with respect to the method for producing a laminate of a sheet-shaped cell culture and a fibrin gel. The method for producing a reinforced laminate may include a step of forming a laminate of a sheet-shaped cell culture and a fibrin gel by the method for producing a laminate of a sheet-shaped cell culture and a fibrin gel mentioned above, a step of dripping a liquid containing thrombin and a liquid containing fibrinogen onto the fibrin gel layer in such a manner that the two liquids are mixed on the fibrin gel layer, and a step of forming a reinforcing portion made of a fibrin gel on the fibrin gel layer by a reaction between fibrinogen and thrombin. Therefore, the method for producing a reinforced laminate may also include the various steps described above with respect to the method for producing a laminate, such as a step of washing the laminate after the step of forming a fibrin gel layer, a step of trimming excess fibrin gel after the step of forming a fibrin gel layer (in the case where a step of washing a laminate is included, after the washing step), further a step of producing a sheet-shaped cell culture.

The dripping of the thrombin liquid and the fibrinogen liquid onto the fibrin gel layer may be performed in any order or may also be simultaneous. For example, the step of dripping a thrombin liquid and a fibrinogen liquid onto a fibrin gel layer is not limited, and encompasses (1) a step in which a thrombin liquid is dripped onto a fibrin gel layer, and then a fibrinogen liquid is dripped onto the dripped thrombin liquid, (2) a step in which a fibrinogen liquid is dripped onto a fibrin gel layer, and then a thrombin liquid is dripped onto the dripped fibrinogen liquid, and (3) a step in which a thrombin liquid and a fibrinogen liquid are simultaneously dripped onto a fibrin gel layer, for example.

The dripping of the thrombin liquid and the fibrinogen liquid onto a fibrin gel layer may be performed using known techniques, such as a syringe or a pipet. As a syringe, for example, a needle-less syringe having a volume of 0.5 mL to 5 mL, a needle-equipped syringe (for example, a syringe equipped with a needle of 18 G to 27 G), the two-component mixing set of the preparation set attached to tissue adhesive BOLHEAL® (equipped with an application nozzle about 1 mm in inner diameter, manufactured by Nipro Corporation), or the two-component mixing set of the preparation set of Beriplast (equipped with an application nozzle, manufactured by Nipro Corporation) can be used. The particle size of droplets of the thrombin liquid or fibrinogen liquid during dripping is not particularly limited, and may be, for example, within a range such that the diameter of droplets adhering to the sheet-shaped cell culture after dripping will be about 0.2 cm to about 2.0 cm. In addition, the weight of droplets of the thrombin liquid or fibrinogen liquid during dripping is not limited, and may be, for example, within a range of, for example, about 10 mg to about 100 mg, about 15 mg to about 50 mg, or about 20 mg to about 30 mg. The particle size and weight of droplets may be suitably adjusted by selecting whether the syringe is equipped with a needle, the gauge of the applied needle, or the shape of the needle tip. The dripping amounts of the thrombin liquid and the fibrinogen liquid and the ratio between the thrombin liquid and fibrinogen liquid dripped are as described above with respect to the reinforced laminate.

The step of forming a reinforcing portion made of a fibrin gel on a fibrin gel layer is not limited, and may be performed, for example, by allowing a laminate to stand for a given period of time after dripping the thrombin liquid and the fibrinogen liquid. The standing time is not limited, and may be, for example, about 1 minute to about 60 minutes, about 2 minutes to about 30 minutes, about 3 minutes to about 20 minutes, or about 4 minutes to about 10 minutes. More specifically, it may be, for example, about 1 minute, about 2 minutes, about 3 minutes, about 4 minutes, about 5 minutes, about 6 minutes, about 7 minutes, about 8 minutes, about 9 minutes, or about 10 minutes, and may particularly be about 5 minutes.

After the step of forming a reinforcing portion made of a fibrin gel, a step of washing the reinforced laminate may be performed. Washing may be performed by adding a predetermined amount of washing liquid to the container containing the reinforced laminate, and then discarding the same. Examples of washing liquids include, but are not limited to, water, physiological saline, various buffers (for example, PBS, and HBSS), and various liquid media (for example, DMEM, MEM, F12, DME, RPMI1640, MCDB (MCDB102, 104, 107, 120, 131, 153, and 199), L15, SkBM, RITC80-7, and DMEM/F12). The washing step can be performed once or more. In addition, the washing liquid added to the container may be discarded immediately, or may also be allowed to stand for a predetermined period of time (for example, without being limited thereto, for example, about 1 minute to about 60 minutes, about 5 minutes to about 30 minutes, or about 10 minutes to about 20 minutes, and particularly about 15 minutes) and then discarded.

The laminate of the disclosure (including the reinforced laminate; the same hereinafter) is useful for the treatment of various diseases associated with tissue abnormality. Thus, in one exemplary embodiment, the laminate of the disclosure is for use in the treatment of a disease associated with tissue abnormality. The laminate of the disclosure is configured such that a biocompatible fibrin gel layer is laminated on one side of a sheet-shaped cell culture. Thus, the other side of the sheet-shaped cell culture is intact, and the fibrin gel is eventually degraded in vivo and disappears. Therefore, the laminate can be applied to tissues and diseases that can be treated with a sheet-shaped cell culture. Treatment target tissues are not limited, and examples thereof include cardiac muscle, cornea, retina, esophagus, skin, joints, cartilage, liver, pancreas, gums, kidney, thyroid gland, skeletal muscle, and middle ear. In addition, treatment target diseases are not limited, and examples thereof cardiac diseases (for example, myocardial damage (myocardial infarction, and cardiac injury), cardiomyopathy (ischemic cardiomyopathy, dilated cardiomyopathy, and dilated phase of hypertrophic cardiomyopathy)), corneal diseases (for example, corneal epithelial stem cell deficiency, corneal damage (thermal/chemical erosion), corneal ulcer, corneal opacity, corneal perforation, corneal scar, Stevens-Johnson syndrome, and ocular pemphigoid), retinal diseases (for example, pigmentary retinopathy, and age-related macular degeneration), esophageal diseases (for example, the prevention of esophageal inflammation or stricture after esophageal surgery (removal of esophageal cancer), skin diseases (for example, skin damage (traumatic injury, thermal burn)), joint diseases (for example, arthritis deformans), cartilage diseases (for example, cartilage damage), hepatic diseases (for example, chronic hepatic diseases), pancreatic diseases (for example, diabetes), dental diseases (for example, periodontosis), renal diseases (for example, renal insufficiency, renal anemia, and renal osteodystrophy), thyroid diseases (for example, hypothyroidism), muscular diseases (for example, muscle damage, and myositis), and middle ear diseases (for example, otitis media).

The usefulness of a sheet-shaped cell culture for these diseases is described in, for example, JP-T-2007-528755, Haraguchi et al., Stem Cells Transl Med., 2012 February; 1 (2): 136-41, Arauchi et al., Tissue Eng Part A., 2009 December; 15 (12): 3943-9, Ito et al., Tissue Eng., 2005 March-April; 11 (3-4): 489-96, Yaji et al., Biomaterials., 2009 February; 30 (5): 797-803, Yaguchi et al., Acta Otolaryngol., 2007 October; 127 (10): 1038-44, Watanabe et al., Transplantation., 2011 Apr. 15; 91 (7): 700-6, Shimizu et al., Biomaterials., 2009 October; 30 (30): 5943-9, Ebihara et al., Biomaterials., 2012 May; 33 (15): 3846-51, and Takagi et al., World J Gastroenterol., 2012 Oct. 7; 18 (37): 5145-50.

The laminate of the disclosure can be applied to a treatment target tissue and used to restore and regenerate the same, and can also be implanted at a site other than the treatment target tissue (for example, subcutaneous tissue) as a source of physiologically active substances, such as hormones (for example, Arauchi et al., Tissue Eng Part A., 2009 December; 15 (12): 3943-9, Shimizu et al., Biomaterials., 2009 October; 30 (30): 5943-9). The laminate of the disclosure can be used for regenerative medicine and thus is also applicable as a product for regenerative medicine. In addition, the laminate of the disclosure can also be used as a graft.

In an exemplary embodiment, the laminate of the disclosure is substantially aseptic. In an exemplary embodiment, the laminate of the disclosure is aseptic. In an exemplary embodiment, the sheet-shaped cell culture contained in the laminate of the disclosure is not genetically engineered. In another exemplary embodiment, the sheet-shaped cell culture contained in the laminate of the disclosure is genetically engineered. Genetic engineering is not limited and may be, for example, the introduction of genes that enhance the viability, engraftment ability, and function of the sheet-shaped cell culture and/or genes useful for the treatment of a disease. Genes to be introduced are not limited, and examples thereof include cytokine genes, such as the HGF gene and the VEGF gene.

Another aspect of the disclosure relates to a pharmaceutical composition containing the laminate of the disclosure. The pharmaceutical composition of the disclosure may contain, in addition to the laminate of the disclosure, various additional components such as pharmacologically acceptable supports, components that enhance the viability, engraftment ability, and/or function of the sheet-shaped cell culture, and other active ingredients useful for the treatment of the target disease. Such additional components may be any known components, and one of ordinary skill in the art is familiar with these additional components. In addition, the pharmaceutical composition of the disclosure can be used together with components that enhance the viability, engraftment ability, and/or function of the sheet-shaped cell culture, and other active ingredients useful for the treatment of the target disease. In an exemplary embodiment, the pharmaceutical composition of the disclosure is for use in the treatment of a disease associated with tissue abnormality. Treatment target tissues and diseases are as described above with respect to the laminate of the disclosure.

Another aspect of the disclosure relates to a method for treating a disease associated with tissue abnormality in a subject, including administering an effective amount of the laminate or pharmaceutical composition of the disclosure to a subject in need of treating a disease associated with tissue abnormality. Tissues and diseases targeted by the treatment method of the disclosure are as described above with respect to the laminate of the disclosure. In addition, in the treatment method of the disclosure, the laminate or pharmaceutical composition of the disclosure can be used together with components that enhance the viability, engraftment ability, and/or function of the sheet-shaped cell culture, and other active ingredients useful for the treatment of the target disease.

The treatment method of the disclosure may further include a step of producing a laminate in accordance with the production method of the disclosure. The treatment method of the disclosure may further include, before the step of producing a laminate, a step of producing a sheet-shaped cell culture and a step of collecting cells or a cell source tissue for producing a sheet-shaped cell culture from a subject. In an exemplary embodiment, the subject from which cells or a cell source tissue is collected is the same individual as the subject to be treated by the administration of the laminate or the pharmaceutical composition. In another exemplary embodiment, the subject from which cells or a cell source tissue is collected is a different individual of the same species as the subject to be treated by the administration of the laminate or the pharmaceutical composition. In another exemplary embodiment, the subject from which cells or a cell source tissue is collected is an individual of a different species from the subject to be treated by the administration of the laminate or the pharmaceutical composition.

In the disclosure, the term "subject" means any individual organism, preferably an individual animal, still more preferably an individual mammal, and yet more preferably an individual human. In the disclosure, the subject may be healthy or may have a certain disease. However, in the case where it is intended to treat a disease associated with tissue abnormality, the term typically means a subject with the disease or at risk of having the disease.

In addition, the term "treatment" encompasses all pharmaceutically acceptable prophylactic and/or therapeutic interventions aimed at the cure, temporary remission, or prevention of a disease, for example. For example, the term "treatment" encompasses various desired medically acceptable interventions including the delay or suspension of the progression of a disease associated with tissue abnormality, the regression or disappearance of the lesion, and the prevention of the occurrence or recurrence of the disease.

In the disclosure, an effective amount is an amount (for example, the size or weight of the laminate) that can suppress the occurrence or recurrence of a disease, alleviate the symptoms, or delay or suspend the progression, for example, and is preferably an amount that prevents the occurrence and recurrence of the disease or cures the disease. In addition, an amount that does not cause an adverse effect exceeding the benefit of administration is preferable. Such an amount can be suitably determined, for example, by a test using experimental animals or disease model animals such as mice, rats, dogs, or pigs, and such a test method is well known to those skilled in the art. In addition, the size of the lesion in the treatment target tissue can be an important index to determine the effective amount.

In accordance with an exemplary embodiment, the administration method may be direct application to a tissue. The administration frequency can be once per treatment. However, in the case where a desired effect is not obtained, it is also possible to perform administration several times. When applied to a tissue, the laminate or pharmaceutical composition of the disclosure may be fixed to the target tissue by a locking means such as a suture or a staple. In the case where the reinforced laminate is used, the locking means may be applied to the reinforcing portion.

The disclosure will be described in further detail with reference to the following examples. However, they show certain specific examples of the disclosure, and the disclosure is not limited thereto.

EXAMPLE 1

Production of Laminate of Fibrin Gel and Sheet-Shaped Cell Culture

Skeletal myoblasts (CD56 positive) cryopreserved in a preservation liquid for cell freezing (MCDB culture medium containing 10% DMSO) were thawed at 37° C., and washed twice using a physiological buffer containing 0.5% serum albumin. $6.0 \times 10^7$ washed cells were suspended in a DMEM culture medium containing 20% human blood serum (10 mL), and seeded on a 10-cm-diameter cell culture dish (UpCell® 10-cm dish, CS3005, manufactured by CellSeed Inc.). After seeding, the cells were cultured in an incubator set at 37° C. and 5% $CO_2$ (BNA-121D, manufactured by Espec Corp.) for 20 hours. After culturing, the culture dish was taken out from the incubator. After confirming the presence of a sheet-shaped cell culture adhering to cover the entire bottom of the culture dish, the culture medium was discarded. Subsequently, the sheet-shaped cell culture was separated from the culture dish by a temperature treatment (allowing to stand at room temperature (20 to 25° C.) for 5 to 30 minutes) and pipetting. The size of the obtained sheet-shaped cell culture was 47 mm×47 mm.

Figure 2:
FIG. 2 is a photograph showing the operation of dripping a fibrinogen liquid onto a sheet-shaped cell culture.
Figure 3:
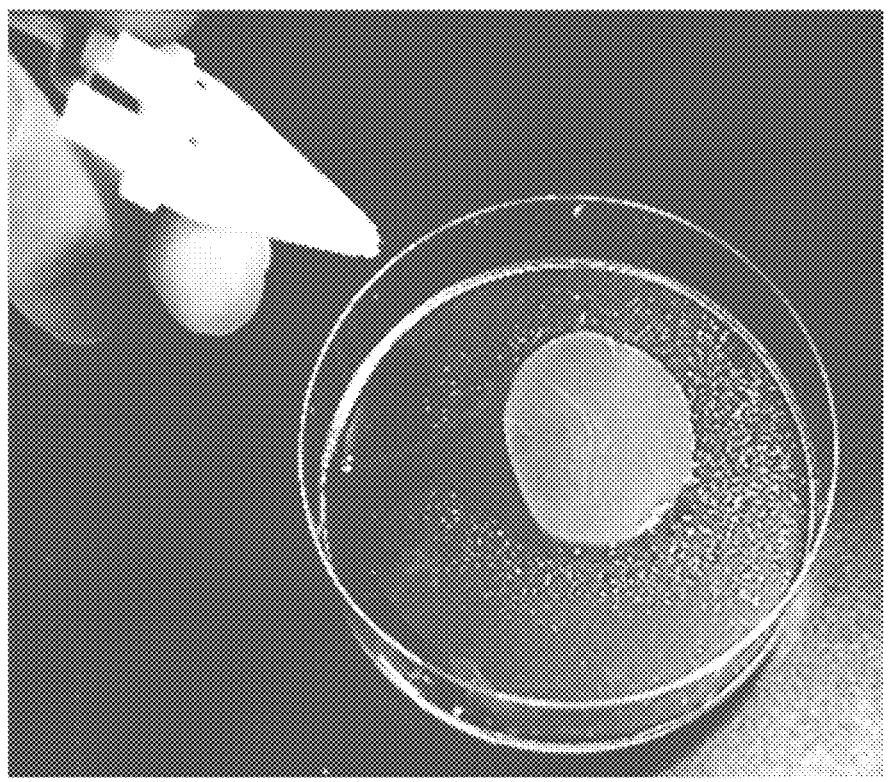
FIG. 3 is a photograph showing the operation of spraying a thrombin liquid onto a sheet-shaped cell culture.

The culture solution in the culture dish was removed, and the sheet-shaped cell culture was shaped as necessary (FIG. 1). Subsequently, onto the sheet-shaped cell culture, 500 μL of a fibrinogen liquid (a solution of the content of Vial 1 (a lyophilized powder of fibrinogen) of tissue adhesive BOLHEAL® (manufactured by Teijin Pharma Ltd.) dissolved in the content of Vial 2 (a fibrinogen solution), fibrinogen concentration: 80 mg/mL; the same hereinafter) was dripped using the two-component mixing set of the preparation set attached to tissue adhesive BOLHEAL® (equipped with an application nozzle about 6 cm in length and about 1 mm in inner diameter, manufactured by Nipro Corporation) (FIG. 2). Next, 800 μL of a thrombin liquid (a solution of the content of Vial 3 (a lyophilized powder of thrombin)) of tissue adhesive BOLHEAL® (manufactured by Teijin Pharma Ltd.) dissolved in the content of Vial 4 (a thrombin solution), thrombin concentration: 250 units/mL; the same hereinafter) was sprayed using BOLHEAL® spray set (manufactured by Akita Sumitomo Bakelite Co., Ltd) from a spray nozzle placed about 7 cm away from the cell sheet at a pressure of 0.03 MPa (FIG. 3). A sheet-shaped cell culture contracts as separated from a culture dish and becomes smaller than the bottom of the culture dish (FIG. 1). Thus, it is estimated that out of 800 μL sprayed, about 500 μL of the thrombin liquid adhered onto the sheet-shaped cell culture. Incidentally, the estimated adhesion amount of the thrombin liquid was calculated as follows. A predetermined amount of thrombin liquid (in this case, 800 μL) was actually sprayed employing a predetermined spray (in the case of this example, BOLHEAL® spray set), spray pressure (in the case of this example, 0.03 MPa), height (in the case of this example, about 7 cm), and spray angle (in the case of this example, 45°), and the weight of the thrombin liquid adhering to a predetermined region (in the case of this example, within a circle about 45 mm in diameter) was measured with an electronic balance and divided by the density of the thrombin liquid.

Figure 4:
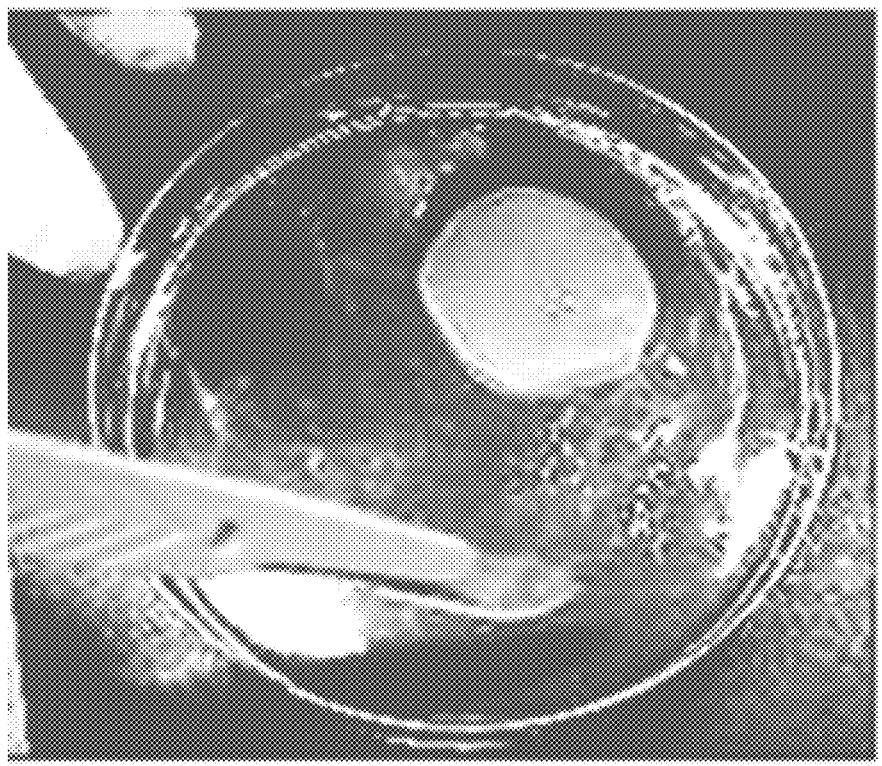
FIG. 4 is a photograph showing the operation of trimming a fibrin gel solidified other than on a sheet-shaped cell culture.

A fibrin gel is formed by a reaction between the fibrinogen liquid and the thrombin liquid. After allowing to stand for about 5 minutes, 24 mL of Hanks' balanced salt solution (HBSS (+), Cat No. 14025, manufactured by Life Technologies Corporation; the same hereinafter) was added to the culture dish and immediately removed, thereby washing the culture dish containing the sheet-shaped cell culture. Unreacted fibrinogen liquid and thrombin liquid can thus be removed. Next, 24 mL of Hanks' balanced salt solution was added again to the culture dish and allowed to stand for about 15 minutes. Subsequently, the solution in the culture dish was removed, the fibrin gel solidified other than on the sheet-shaped cell culture was trimmed with a scalpel (FIG. 4), and a laminate of the fibrin gel and the sheet-shaped culture was isolated (Laminate 1). The isolated laminate was stored until use in a culture dish filled with 24 mL of Hanks' balanced salt solution.

Laminate 2 was produced by the same procedure except that the dripping amount of the fibrinogen liquid was 300 μL, and the spraying amount of the thrombin liquid was about 600 μL (estimated adhesion amount: about 300 μL), Laminate 3 was produced by the same procedure except that the dripping amount of the fibrinogen liquid was 300 μL, and the spraying amount of the thrombin liquid was about 900 μL (estimated adhesion amount: about 450 μL), Laminate 4 was produced by the same procedure except that the dripping amount of the fibrinogen liquid was 300 μL, and the spraying amount of the thrombin liquid was about 300 μL (estimated adhesion amount: about 100 μL), and Laminate 5 was produced by the same procedure except that the dripping amount of the fibrinogen liquid was 500 μL, and the spraying amount of the thrombin liquid was about 500 μL (estimated adhesion amount: about 180 μL).

In addition, for comparison, an attempt was made to produce a laminate of a fibrin gel and a sheet-shaped cell culture by a technique of simultaneously spraying a fibrinogen liquid and a thrombin liquid.

Figure 5:
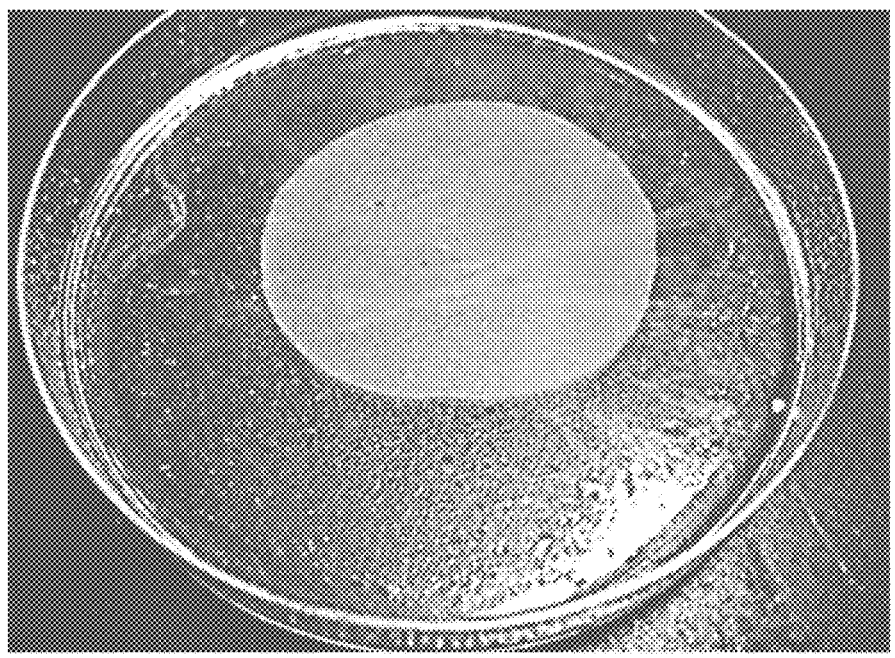
FIG. 5 is a photograph showing a sheet-shaped cell culture after simultaneously spraying a fibrinogen liquid and a thrombin liquid.
Figure 6:
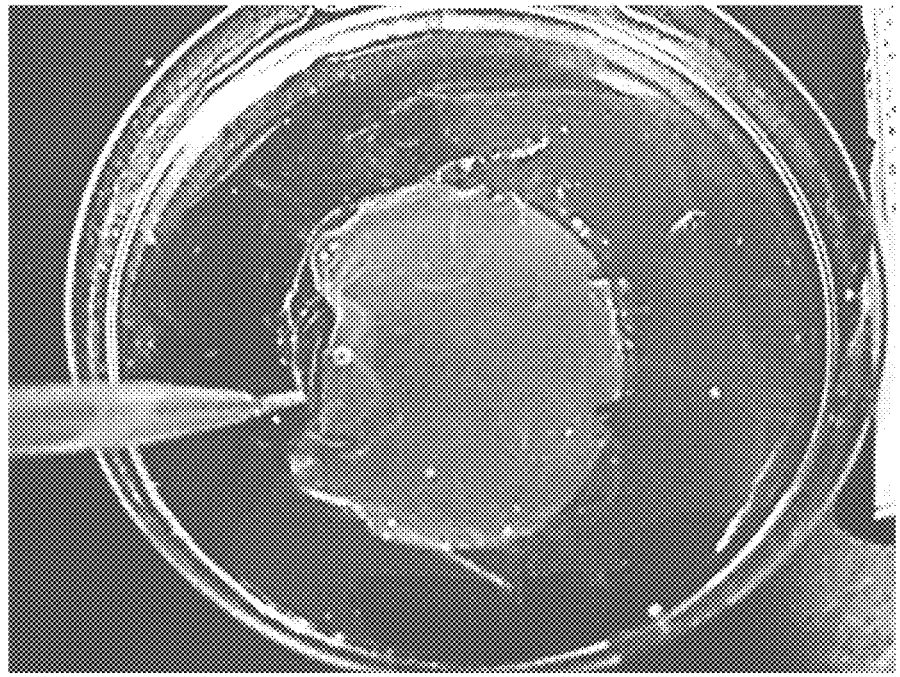
FIG. 6 is a photograph showing the failure of isolation of a laminate of a sheet-shaped cell culture and a fibrin gel obtained by simultaneously spraying a fibrinogen liquid and a thrombin liquid.

In the same manner as for Laminate 1, a sheet-shaped cell culture was formed and separated from the culture dish. The culture solution in the culture dish was removed, and the sheet-shaped cell culture was shaped as necessary (FIG. 1). Subsequently, 800 μL of a fibrinogen liquid and 800 μL of a thrombin liquid were simultaneously sprayed onto the sheet-shaped cell culture using BOLHEAL® spray set (manufactured by Akita Sumitomo Bakelite Co., Ltd) from a spray nozzle placed about 7 cm away from the cell sheet at a pressure of 0.03 MPa (the estimated adhesion amounts to the sheet-shaped cell culture were each about 500 μL). After allowing to stand for about 5 minutes, 24 mL of Hanks' balanced salt solution was added to the culture dish and immediately removed, thereby washing the culture dish containing the sheet-shaped cell culture. Next, 24 mL of Hanks' balanced salt solution was added again to the culture dish and allowed to stand for about 15 minutes, and then solution in the culture dish was removed (FIG. 5). The fibrin gel solidified other than on the sheet-shaped cell culture was trimmed with a scalpel as an attempt to isolate a laminate of the fibrin gel and the sheet-shaped cell culture. However, the fibrin gel came off the sheet-shaped cell culture, and a laminate was not obtained (FIG. 6).

EXAMPLE 2

Evaluation of Laminate of Fibrin Gel and Sheet-Shaped Cell Culture

Figure 7:
FIG. 7 is a photograph of a laminate of the disclosure placed on an intestinal spatula.

Laminates 1 to 5 obtained in Example 1 were evaluated in terms of size, weight, strength, thickness, operability, and properties. Size was measured with a ruler, weight was measured with an electronic non-automatic scale (AT201, manufactured by Mettler-Toledo), and thickness was measured with a dial thickness gauge (SM-124, manufactured by Teclock Corporation). Strength was measured as follows. First, a laminate extended in a liquid was scooped up with an intestinal spatula made of stainless steel (45 mm in width; the same hereinafter) and placed out of the liquid with the laminate adhering to the surface of the intestinal spatula. A suture equipped with a needle (6-0 proline) was inserted between the laminate and the intestinal spatula, and passed through the laminate from the lower surface to the upper surface. Both ends of the thread were tied together to form a ring, which was then connected to a gauge (a general-purpose digital force gage, FGC-1B, manufactured by Nidec-Shimpo Corporation). The thread locked to the laminate was horizontally pulled through the gauge, and the maximum load before the laminate broke (tensile breaking load) was measured. Measurement was performed at three different points on a laminate (n=3). Operability was comprehensively evaluated based on ease of operation in the operation of placing a submerged laminate on an intestinal spatula (FIG. 7) and transferring the same to the side of a bottle simulating the heart (ease of placement on the intestinal spatula, resistance to falling from the intestinal spatula during transfer, and ease of transfer from the intestinal spatula to the bottle), and the condition of the laminate (whether wrinkling or tearing occurs during the operation). Operability was rated on a five-point scale from 5 (the highest) to 1 (the lowest). For properties, the condition of a laminate observed during the evaluation of operability was qualitatively evaluated. In addition, for comparison, a sheet-shaped cell culture having no fibrin gel laminated (produced under the same conditions as for Laminate 1) was also subjected to the same evaluation. The results are shown in Table 1.

sheet-shaped cell cultures laminated were produced, and evaluated in the same manner as above. The results are shown in Table 2. Incidentally, the formation of a sheet-shaped cell culture was performed in a 3.5-cm-diameter cell culture dish (UpCell® 3.5-cm dish, manufactured by CellSeed Inc.). The dry weight of a laminate was determined by weighing a freeze-dried laminate with an electronic balance. Water content was determined by the following equation: water content=(wet weight of laminate−dry weight of laminate)/wet weight of laminate×100(%). In addition, the lamination of sheet-shaped cell cultures was performed as follows. First, a support (CellShifter™, manufactured by

TABLE 1

Evaluation Results of Laminates 1 to 5

|  | Laminate 1 | Laminate 2 | Laminate 3 | Laminate 4 | Laminate 5 | Sheet-Shaped Cell Culture |
|---|---|---|---|---|---|---|
| FN:TN (μL)* | 500:500 | 300:300 | 300:450 | 300:100 | 500:180 | — |
| FN:TN Ratio** | 1:1 | 1:1 | 1:1.5 | 3:1 | 3:1 | — |
| Size (mm) | 45 × 42 | 43 × 42 | 50 × 46 | 42 × 45 | 45 × 40 | 43 × 41 |
| Weight (g) | 1.92995 | 1.26149 | 1.24936 | 0.98233 | 1.5484 | — |
| Strength (N) (n = 3) | 0.047 | 0.020 | 0.023 | 0.033 | 0.043 | 0.007 |
| Thickness (mm) | 1.250 | 0.467 | 0.433 | 0.615 | 1.337 | 0.073 |
| Operability | 5 | 4 | 3 | 1 | 1 | — |
| Properties |  | Flexible and moderately adhesive |  | Rigid and slippery |  | — |

*FN represents the dripping amount of fibrinogen liquid, and TN represents the estimated adhesion amount of thrombin liquid.
**The ratio between the dripping amount of fibrinogen liquid and the estimated adhesion amount of thrombin liquid.

The results in Table 1 show that all the laminates have much higher strength than does the sheet-shaped cell culture having no fibrin gel laminated, and also that an increase in the amount of fibrinogen liquid leads to an increase in the weight, strength, and thickness of the resulting laminate. In addition, although all the laminates allowed for the simulated implantation operation, there was a tendency that operability improved as the volume ratio between the fibrinogen liquid and thrombin liquid adhering to a sheet-shaped cell culture approached 1:1.

By the same method as for Laminate 1, Laminates 6 to 9 that are different in the number of cells, and the number of CellSeed Inc.) was placed on a sheet-shaped cell culture without introducing air bubbles. The support having adhering thereto the sheet-shaped cell culture was peeled from the end to recover the sheet-shaped cell culture together with the support, and then placed on another sheet-shaped cell culture after removing the culture medium. After allowing to stand at 37° C. for about 30 minutes, and after confirming that the sheet-shaped cell cultures adhered to each other, the support was removed from the laminated sheet-shaped cell cultures. As necessary, the same procedure was repeated to perform further lamination.

TABLE 2

Evaluation Results of Laminates 6 to 9

|  | Laminate 6 | Laminate 7 | Laminate 8 | Laminate 9 |
|---|---|---|---|---|
| Number of Seeded Cells (per sheet) | $9.3 \times 10^6$ | $9.3 \times 10^6$ | $4.56 \times 10^6$ | $4.56 \times 10^6$ |
| Number of Laminated Sheets | 1 | 1 | 4 | 3 |
| Size of Sheet-Shaped Cell Culture (mm) | 13 × 11 | 13 × 12 | 13 × 12 | 13 × 11 |
| Weight of Sheet-Shaped Cell Culture (g) | 0.0847 | 0.04073 | 0.06468 | 0.04864 |
| FN:TN (μL)* | 25:25 | 50:50 | 50:50 | 50:50 |
| Size of Laminate (mm) | 16 × 15 | 18 × 13 | 18 × 13 | 15 × 13 |
| Wet Weight of Laminate (g) | 0.13878 | 0.25828 | 0.15574 | 0.14036 |
| Strength of Laminate (N) | 0.02 | 0.06 | 0.08 | 0.07 |
| Thickness of Laminate (mm) | 0.31 | 0.27 | 0.37 | 0.35 |
| Dry Weight of Laminate (g) | 0.00184 | 0.00422 | 0.00534 | 0.00428 |
| Water Content (%) | 98.67416 | 98.36611 | 96.57121 | 96.95070 |

*FN represents the dripping amount of fibrinogen liquid, and TN represents the estimated adhesion amount of thrombin liquid.

The results in Table 2 show that the contribution of a fibrin gel to the weight and strength of a laminate is greater than that of the lamination of sheet-shaped cell cultures.

EXAMPLE 3

Production of Laminate Having Reinforcing Portion

Figure 8:
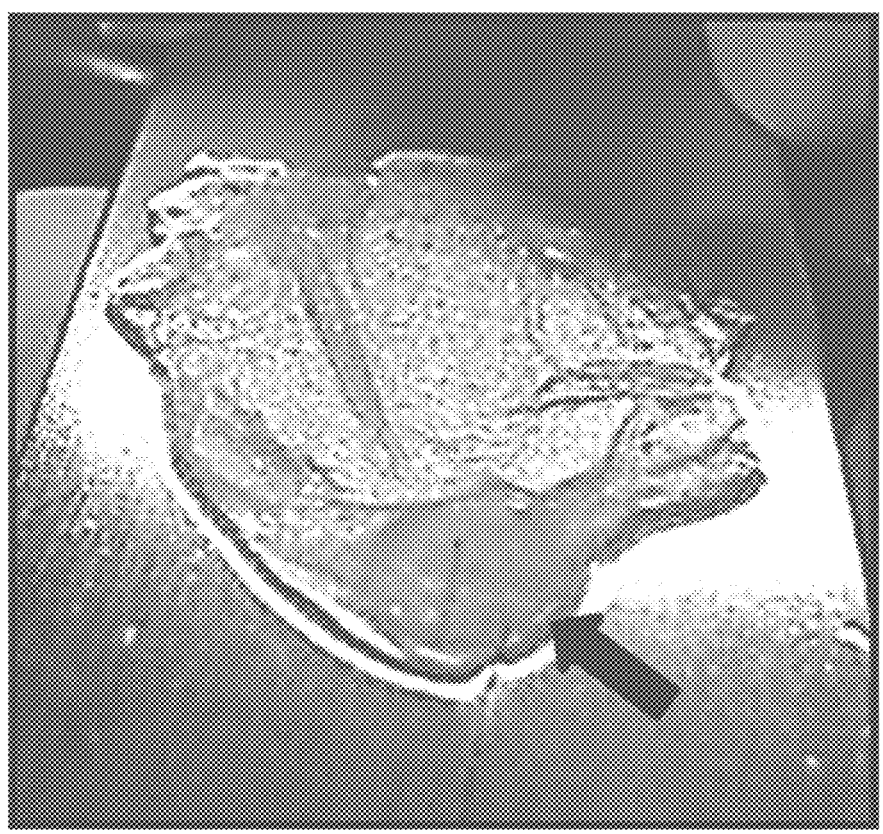
FIG. 8 is a photograph showing a laminate having a reinforcing portion of the disclosure in accordance with an exemplary embodiment, and wherein the black arrow indicates the reinforcing portion, and it can be seen that a suture is passing through the center of the reinforcing portion.

Onto an end of Laminate 2, 50 μL of a thrombin liquid was dripped, and then 50 μL of a fibrinogen liquid was dripped. After allowing to stand for 5 minutes, 24 mL of Hanks' balanced salt solution was added to the culture dish, and unreacted fibrinogen and thrombin were removed. A reinforcing portion was thus formed on Laminate 2. Incidentally, the thrombin liquid and fibrinogen liquid used were the same as those used for the formation of a fibrin gel of a non-reinforcing portion. In addition, onto an end of Laminate 3, 100 μL of a thrombin liquid was dripped, and then 100 μL of a fibrinogen liquid was dripped, thereby forming a reinforcing portion in the same manner (FIG. 8). Strength at the reinforcing portion of Laminate 2 and that of Laminate 3, each provided with a reinforcing portion, were evaluated in the same manner as in Example 2. The results are shown in Table 3.

TABLE 3

Evaluation Results of Reinforcing Portions of Laminates 2 and 3

|  |  | Laminate 2 | Laminate 3 |
|---|---|---|---|
| Dripping Amount to Reinforcing Portion (FN:TN, μL) | | 50:50 | 100:100 |
| Strength of Laminate (N) | Non-reinforcing portion | 0.020 | 0.023 |
|  | Reinforcing portion | 0.09 | 0.17 |

By the same method as above, Laminate 10 having a reinforcing portion was produced using a 3.5-cm-diameter cell culture dish, and evaluated in the same manner as above. The results are shown in Table 4.

TABLE 4

Evaluation Results of Laminate 10

|  |  | Laminate 10 |
|---|---|---|
| Number of Seeded Cells | | $4.56 \times 10^6$ |
| Size of Sheet-Shaped Cell Culture (mm) | | 15 × 11 |
| Weight of Sheet-Shaped Cell Culture (g) | | 0.03558 |
| FN:TN (μL) | Non-reinforcing portion* | 50:50 |
|  | Reinforcing portion** | 25:25 |
| Size of Laminate (mm) | | 16 × 12 |
| Wet Weight of Laminate (g) | | 0.13837 |
| Strength of Laminate (N) | Non-reinforcing portion | 0.02 |
|  | Reinforcing portion | 0.17 |
| Thickness of Laminate (mm) | Non-reinforcing portion | 0.29 |
|  | Reinforcing portion | 1.04 |
| Dry Weight of Laminate (g) | | 0.00508 |
| Water Content (%) | | 96.32868 |

*FN represents the dripping amount of fibrinogen liquid, and TN represents the estimated adhesion amount of thrombin liquid.
**FN represents the dripping amount of fibrinogen liquid, and TN represents the dripping amount of thrombin liquid.

The results shown in Tables 3 and 4 show that a reinforcing portion can have strength that is about 4.5 to 8.5 times that of a non-reinforcing portion. It is also shown that the strength of a reinforcing portion is correlated with the amounts of thrombin liquid and fibrinogen liquid dripped for the formation of the reinforcing portion.

EXAMPLE 4

Fixing of Laminate with Suture

Figure 9:
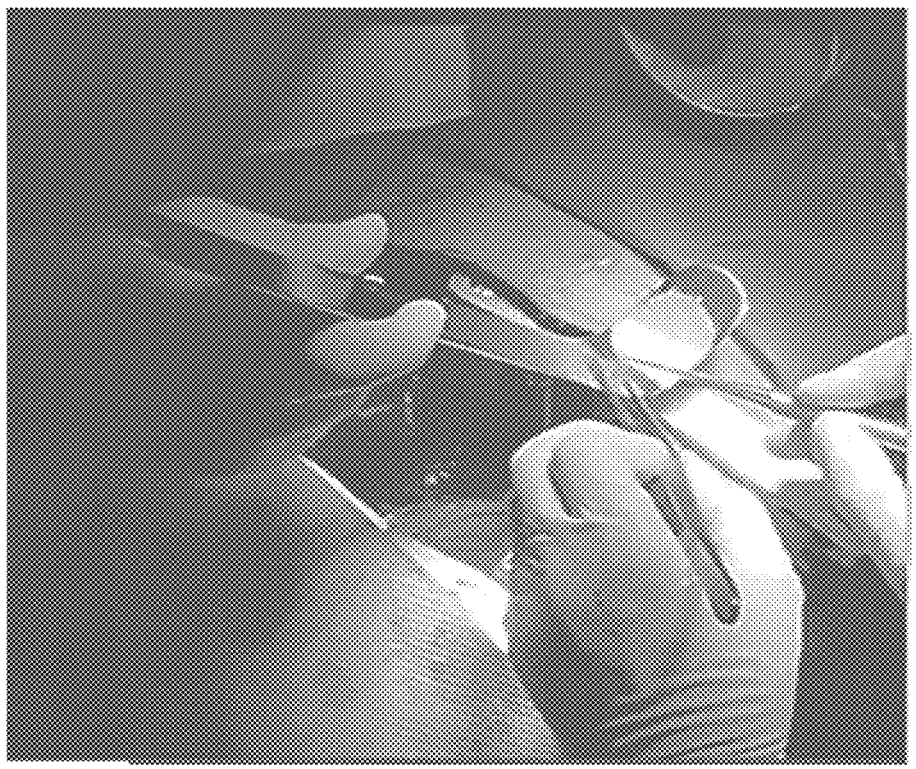
FIG. 9 is a photograph showing the operation of hanging a suture on a laminate of the disclosure placed on an intestinal spatula.
Figure 10:
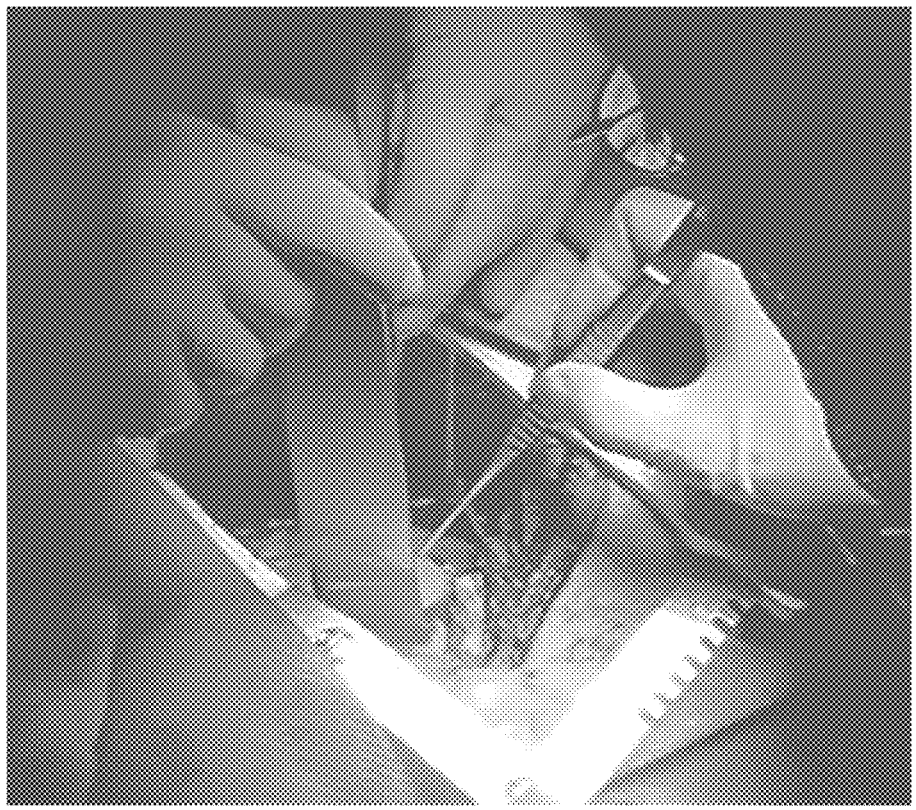
FIG. 10 is a photograph showing the operation of transferring a laminate of the disclosure from an intestinal spatula to an implantation site.
Figure 11:
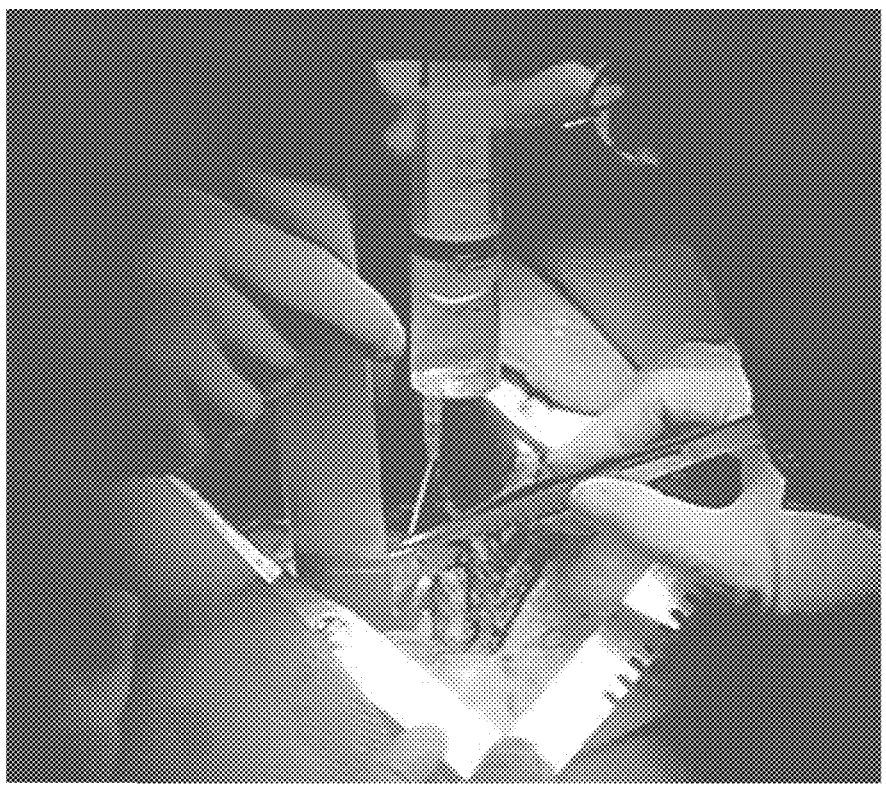
FIG. 11 is a photograph showing the operation of transferring a laminate of the disclosure from an intestinal spatula to an implantation site.
Figure 12:
FIG. 12 is a photograph showing the detachment of a suture from a laminate of the disclosure transferred to an implantation site.
Figure 13:
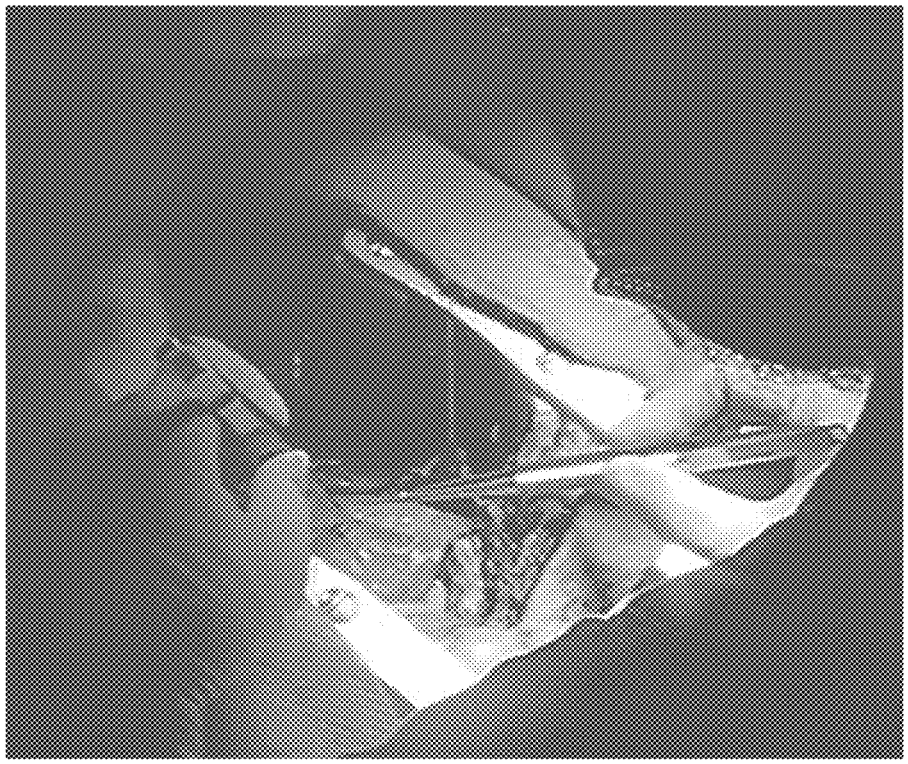
FIG. 13 is a photograph showing the resuturing of a laminate of the disclosure to an implantation site.

For the evaluation of the operability of a laminate during implantation, the following test was performed using a laminate produced under the same conditions as for Laminate 3 (dripping 300 μL of a fibrinogen liquid+spraying about 100 μL of a thrombin liquid (estimated adhesion amount)) (n=2). A submerged laminate was placed on an intestinal spatula, a suture (7-0 proline) was hung on the end of the laminate (FIG. 9), and the laminate was transferred from the intestinal spatula to a surgically exposed pig's heart (FIGS. 10 to 11) and fixed with the suture. After the implantation of the laminate, the chest was closed, and the subsequent condition of the animal was observed. Five laminates were implanted per pig. In each test, in one of the five laminates implanted, after the laminate was fixed to the surface of the heart with a suture, the laminate could not withstand the tension of the suture, tearing occurred from the pass-through part, whereby the suture was detached (FIG. 12), and suturing was performed again (FIG. 13). However, the laminates were all eventually fixed to the surface of the heart.

Figure 14:
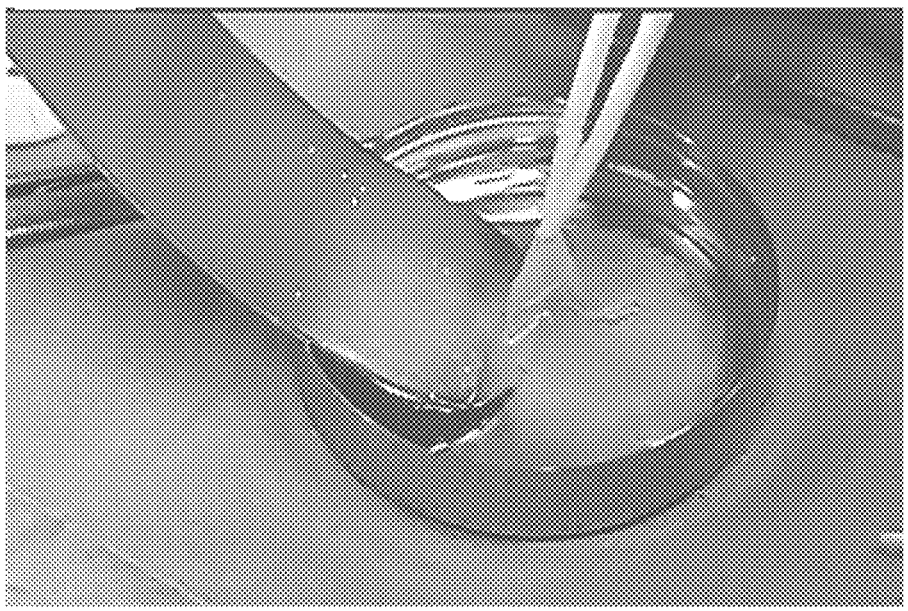
FIG. 14 is a photograph showing the operation of transferring a laminate of the disclosure to an intestinal spatula.
Figure 15:
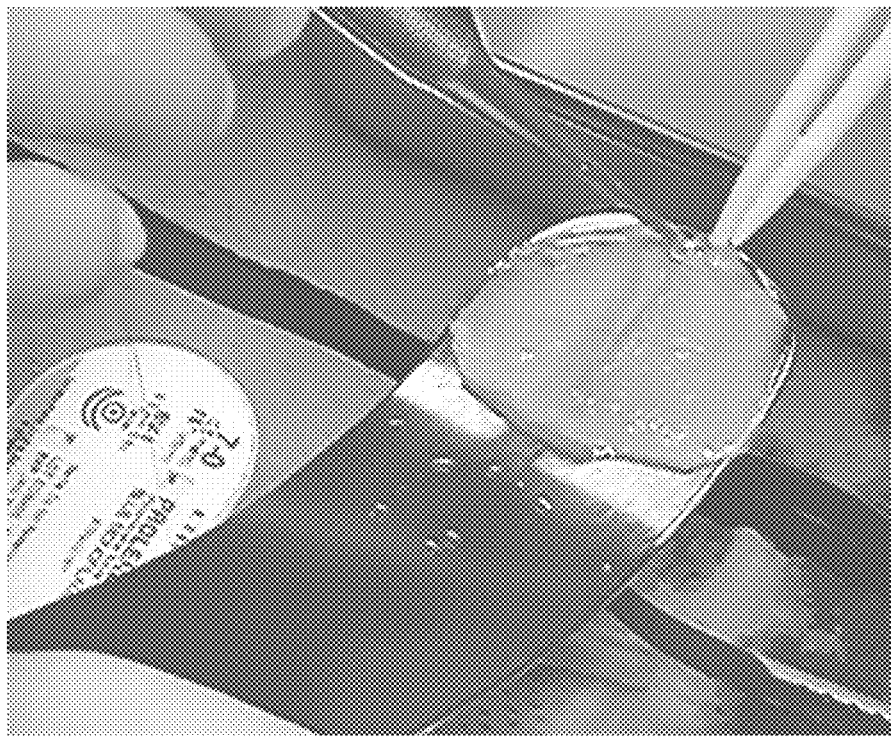
FIG. 15 is a photograph showing the operation of hanging a suture on a marginal part of a laminate of the disclosure.
Figure 16:
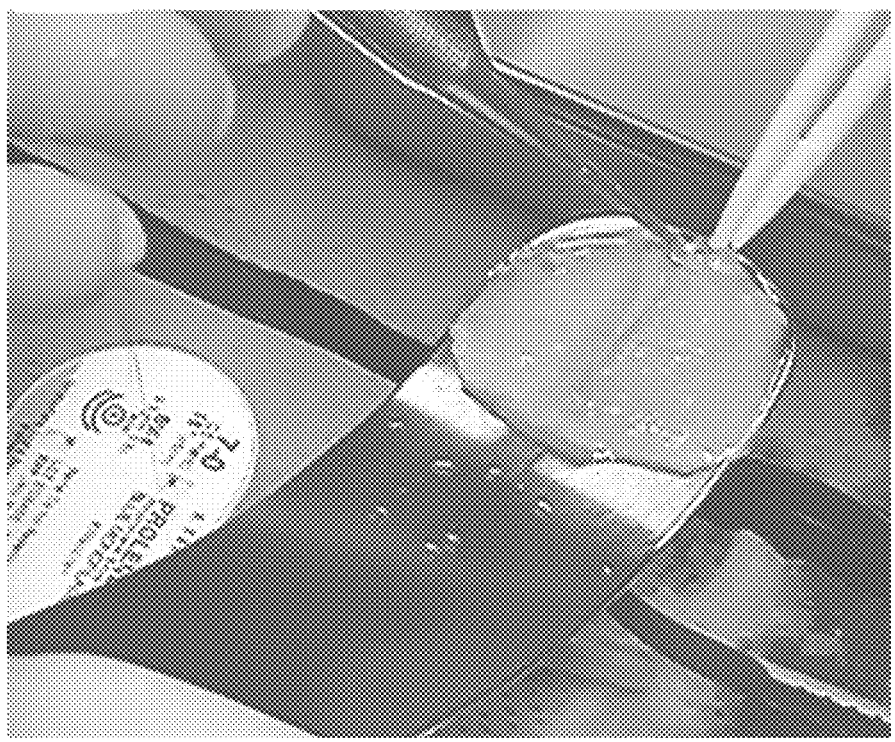
FIG. 16 is a photograph showing the operation of hanging a suture on a marginal part of a laminate of the disclosure.
Figure 17:
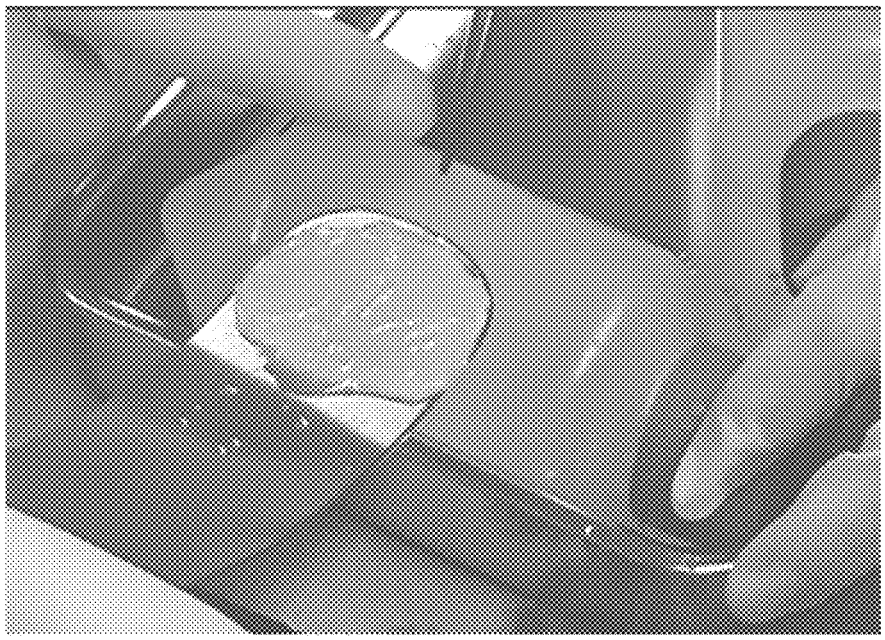
FIG. 17 is a photograph showing the operation of hanging a suture on a marginal part of a laminate of the disclosure.
Figure 18:
FIG. 18 is a photograph showing a laminate of the disclosure that has been transferred to the side of a bottle.

In addition, the following test was performed using a laminate produced under the same conditions as for Laminate 1 (dripping 500 μL of a fibrinogen liquid+spraying about 500 μL of a thrombin liquid (estimated adhesion amount)). A submerged laminate was placed on an intestinal spatula (FIG. 14), a suture (7-0 proline) was hung on a marginal part (FIGS. 15 to 17), and the operation of transferring the same to the side of a bottle simulating the heart (FIG. 18) was performed. The laminate had moderate flexibility and stickiness, was easy to place on an intestinal spatula, allowed for smooth transfer from the intestinal spatula to the bottle, and also fitted well on the curving surface of the bottle. In addition, during the series of operations, the suture remained firmly hung on the laminate, and it did not happen that the laminate was broken to detach the suture.

EXAMPLE 5

Treatment with Laminate

Laminates were used to treat human patients having serious myocarditis (ischaemic cardiomyopathy, and dilated cardiomyopathy). A laminate was produced under the same conditions as for Laminate 1 (dripping 500 μL of a fibrinogen liquid+spraying about 500 μL of a thrombin liquid (estimated adhesion amount)). The laminate was placed on an intestinal spatula, transferred onto the patient's heart exposed by thoracotomy, and fixed with a suture. The chest was then closed, and the condition of the patient was observed. In all the patients, improvement was seen in cardiac performance, exercise tolerance, QOL, morbidity, and prognosis.

The detailed description above describes a method for producing a laminate of a sheet-shaped cell culture and a fibrin gel, a laminate produced by the method, a pharmaceutical composition containing the laminate, and a method for treating a disease using the laminate. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for producing a laminate of a fibrin gel and a sheet-shaped cell culture, comprising:
dripping a liquid containing fibrinogen onto an upper surface of a sheet-shaped cell culture;
spraying a liquid containing thrombin onto the surface after dripping the liquid containing fibrinogen onto the surface; and
forming a fibrin gel layer on the surface by a reaction between the fibrinogen and the thrombin.

2. The method according to claim 1, further comprising:
after forming the fibrin gel layer, washing the laminate.

3. The method according to claim 2, further comprising:
after forming the fibrin gel layer, trimming excess fibrin gel.

4. The method according to claim 1, further comprising:
after forming the fibrin gel layer, trimming excess fibrin gel.

5. A laminate of a fibrin gel and a sheet-shaped cell culture produced by a method comprising:
dripping a liquid containing fibrinogen onto an upper surface of a sheet-shaped cell culture;
spraying a liquid containing thrombin onto the surface after dripping the liquid containing fibrinogen onto the surface; and
forming a fibrin gel layer on the surface by a reaction between the fibrinogen and the thrombin.

6. The laminate of a fibrin gel and a sheet-shaped cell culture produced by the process according to claim 5, wherein the laminate is washed after the fibrin gel layer is formed.

7. The laminate of a fibrin gel and a sheet-shaped cell culture produced by the method according to claim 6, wherein excess fibrin gel is trimmed after the fibrin gel layer is formed.

8. The laminate of a fibrin gel and a sheet-shaped cell culture produced by the method according to claim 5, wherein excess fibrin gel is trimmed after the fibrin gel layer is formed.

9. A pharmaceutical composition comprising the laminate according to claim 5.

10. The pharmaceutical composition according to claim 9, for treating a disease associated with tissue abnormality.

11. A method for treating a disease associated with tissue abnormality in a subject, comprising:
administering an amount of a laminate, the laminate comprising a fibrin gel and a sheet-shaped cell culture, and wherein the laminate is produced by a method comprising:
dripping a liquid containing fibrinogen onto an upper surface of a sheet-shaped cell culture;
spraying a liquid containing thrombin onto the surface of the sheet-shaped cell culture after dripping the liquid containing fibrinogen onto the surface; and
forming a fibrin gel layer on the surface by a reaction between the fibrinogen and the thrombin.

12. A method for treating a disease associated with tissue abnormality in a subject, comprising:
administering an amount of a pharmaceutical composition to a subject in need of treating a disease associated with tissue abnormality the pharmaceutical composition comprising a laminate comprising a fibrin gel and a sheet-shaped cell culture, and wherein the laminate is produced by a method comprising:
dripping a liquid containing fibrinogen onto an upper surface of a sheet-shaped cell culture;
spraying a liquid containing thrombin onto the surface of the sheet-shaped cell culture after dripping the liquid containing fibrinogen onto the surface; and
forming a fibrin gel layer on the surface by a reaction between the fibrinogen and the thrombin.

13. The method according to claim 11, wherein:
the sheet-shaped cell culture is prepared on a culture dish; and
the laminate of the fibrin gel and the sheet-shaped cell culture are transferred onto a subject's heart.

14. The method according to claim 11, wherein the laminate further comprises:
a reinforcing portion made of a fibrin gel, the reinforcing portion formed by laminating the fibrin gel on the fibrin gel layer of the laminate of the sheet-shaped cell culture and the fibrin gel.

15. The method according to claim 11, comprising:
suturing the laminate of the fibrin gel and the sheet-shaped cell culture to the tissue abnormality in the subject.

16. The method according to claim 11, comprising:
a ratio of fibrinogen to thrombin adhering to the laminate of about 8:5 to about 8:75.

17. The method according to claim 12, wherein:
the sheet-shaped cell culture is prepared on a culture dish;
the laminate of the fibrin gel and the sheet-shaped cell culture are transferred onto a subject's heart; and
suturing the laminate of the fibrin gel and the sheet-shaped cell culture to the tissue abnormality in the subject.

18. The method according to claim 12, wherein the laminate further comprises:
a reinforcing portion made of a fibrin gel, the reinforcing portion formed by laminating the fibrin gel on the fibrin gel layer of the laminate of the sheet-shaped cell culture and the fibrin gel.

19. The method according to claim 12, comprising:
a ratio of fibrinogen to thrombin adhering to the laminate of about 8:5 to about 8:75.

* * * * *